US007790410B2

(12) United States Patent
Yu et al.

(10) Patent No.: US 7,790,410 B2
(45) Date of Patent: Sep. 7, 2010

(54) METHOD AND APPARATUS FOR DETERMINING HEMOCOMPATIBILITY

(75) Inventors: Liming Yu, New York, NY (US); Aaron Dulgar-Tulloch, Cohoes, NY (US)

(73) Assignee: General Electric Company, Niskayuna, NY (US)

( * ) Notice: Subject to any disclaimer, the term of this patent is extended or adjusted under 35 U.S.C. 154(b) by 118 days.

(21) Appl. No.: 12/110,104

(22) Filed: Apr. 25, 2008

(65) Prior Publication Data

US 2009/0269790 A1      Oct. 29, 2009

(51) Int. Cl.
*C12Q 1/56*  (2006.01)
(52) U.S. Cl. .......................... 435/13; 435/7.1; 435/69.6
(58) Field of Classification Search ....................... None
See application file for complete search history.

(56) References Cited

U.S. PATENT DOCUMENTS

| 2008/0003691 | A1 | 1/2008 | Tachibana et al. |
| 2008/0039337 | A1 | 2/2008 | Nonaka et al. |

FOREIGN PATENT DOCUMENTS

| EP | 0345811 | * | 9/1989 |
| WO | WO8606489 | | 11/1986 |
| WO | WO2007010240 | | 1/2007 |

OTHER PUBLICATIONS

Schluter et al. Analytical Chem. 2007 vol. 79, p. 1251-1255.*
Kenyon M. Evans-Nguyen, Lauren R. Tolles, Oleg V. Gorkun, Susan T. Lord, and Mark H. Schoenfisch; Interaction of Thrombin with Fibrinogen Absorbed on Methyl-, Hydroxyl-, Amine-, and Carboxyl-Terminated Self-Assembled Monolayers; American Chemical Society; pp. 15561-15568; vol. 44, 2005.
Patel, R. et al., "Surface Adsorption and Fibrinogen Interactions with Hirudin-Thrombin Complex", Journal of Biomedical Materials Research, vol. 32, Issue 1, pp. 1-2, 1994.
Greer, C. et al., "Surface-dependent Fibrinopeptide A Accessibility to Thrombin", (Abstract) ACTA Biomaterials, vol. 3, Issue 5, Sep. 2007, pp. 1-3.
Celikel, R. et al., "Modulation of Alpha-Thrombin Function by Distinct Interactions with Platelet Glycoprotein IbAlpha", Science, Jul. 2003, vol. 301. No. 5630, pp. 1-12.
Patel, R. et al., "Surface Adsorption and Fibrinogen Interactions with Hirudin-Thrombin Complex", Journal of Biomedical Materials Research, vol. 32, Issue 1, pp. 1-2.
Stubbs, M. et al., "The Interaction of Thrombin with Fibrinogen", European Journal of Biochemistry, vol. 206, Issue 1, pp. 1-2, Mar. 3, 2005 .

* cited by examiner

*Primary Examiner*—Jacob Cheu
(74) *Attorney, Agent, or Firm*—Fletcher Yoder

(57) ABSTRACT

Provided herein are techniques for screening materials for hemocompatibility. Hemocompatible materials may be advantageous when incorporated into devices that may come into direct contact with blood or other bodily fluids. Such techniques take advantage of conformational changes in fibrinogen when adsorbed onto certain materials. As a result of conformational changes, the fibrinogen has altered responsiveness to cleavage by thrombin. Accordingly, the products of thrombin cleavage of fibrinogen may be assessed to determine the hemocompatibility of a material.

20 Claims, 5 Drawing Sheets

METHOD AND APPARATUS FOR DETERMINING HEMOCOMPATIBILITY

BACKGROUND

The invention relates generally to assessing the hemocompatibility of a material. More specifically, the invention relates to an assay for detecting conformational changes in adsorbed fibrinogen as a measurement of material hemocompatibility.

In the field of medical devices, many devices are designed to come into direct contact with patient blood. Such devices may include in-dwelling devices such as catheters and stents, as well as extra-corporeal devices such as oxygenators and apheresis units. Devices in contact with human blood may trigger certain biological responses, such as inflammation or coagulation of the blood. Such coagulation of the blood may be mediated by certain blood proteins, such as fibrinogen.

Modifications in the conformation of adsorbed fibrinogen may lead to the exposure of certain internal epitopes. Exposure of such epitopes may result in platelet adhesion or thrombosis. Therefore, a sensitive and robust test for detecting conformation changes of fibrinogen adsorbed on material surfaces may be beneficial for the screening and development of novel biomaterials.

The currently available analytical technologies for assessing the conformation of adsorbed fibrinogen are complicated, expensive, time-intensive, and of limited sensitivity. As such, these techniques are unsuitable for high-throughput biomaterial screening.

BRIEF DESCRIPTION

Changes in the conformation of proteins, such as fibrinogen, may also change the efficiency of their cleavage by native proteases, such as thrombin. As such, the present techniques measures the efficiency of the fibrinogen cleavage by quantifying its cleavage products, fibrinopeptide A (FPA) and/or fibrinopeptide B (FPB), and utilizes this as a surrogate marker for conformational changes, thus predicting material hemocompatibility.

The present techniques provide a method for screening candidate materials for hemocompatibility. A hemocompatible material may refer to a material that does not induce thrombosis, fibrin formation, and/or platelet adhesion when in contact with blood or blood products. In another embodiment, a hemocompatible material may be a material that has reduced or substantially lower fibrinogen adsorption as compared to a material that is not hemocompatible. Still another embodiment involves a hemocompatible material that causes fewer conformational changes in adsorbed fibrinogen as compared to a material that is not hemocompatible.

The present techniques provide a method of screening materials for hemocompatibility that includes contacting a candidate material with fibrinogen; contacting the candidate material with thrombin; determining a presence or level of a fibrinogen cleavage product; and determining if the candidate material is hemocompatible based on the presence or level of the fibrinogen cleavage product.

The present techniques also provide a method of screening materials for hemocompatibility that includes adsorbing fibrinogen with a candidate material; cleaving the fibrinogen with thrombin to yield a fibrinogen cleavage product; binding the fibrinogen cleavage product with signal generator; and detecting the signal emitted by the signal generator.

The present techniques also provide a high-throughput screening method for hemocompatibility that includes contacting a plurality of candidate materials with fibrinogen; contacting the plurality of candidate materials with thrombin; determining a presence or level of a fibrinogen cleavage product for each of the plurality of candidate materials; and identifying which of the plurality of candidate materials are hemocompatible based on the presence or level of the fibrinogen cleavage product.

The present techniques also provide a method of making a medical device that includes providing a hemocompatible material and forming a medical device from the hemocompatible material. The hemocompatible material has been identified by contacting a candidate material with fibrinogen; contacting the candidate material with thrombin; determining a presence or level of a fibrinogen cleavage product; and determining if the candidate material is hemocompatible based on the presence or level of the fibrinogen cleavage product.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present techniques provide methods for screening the hemocompatibility of a material. Additionally, the present techniques may also be appropriate for confirming the hemocompatibility of a material assessed by alternate methods. These techniques take advantage of conformational changes that may occur in fibrinogen when this protein is adsorbed on certain materials. Adsorption of fibrinogen onto a material with a corresponding conformational change may prevent cleavage of fibrinogen by thrombin. When thrombin cleavage is prevented or reduced, the cleavage products of fibrinogen, such as fibrinopeptide A or fibrinopeptide B, are also reduced.

The present techniques provide an advantage over previous techniques for evaluating materials by measuring fibrinogen conformational changes upon adsorption as a marker for hemocompatibility. While fibrinogen adsorption onto a material may influence the formation of fibrin on the surface of the material, which may ultimately influence platelet adhesion and coagulation, fibrinogen adsorption alone may not be directly related to platelet adhesion.

Figure 1:
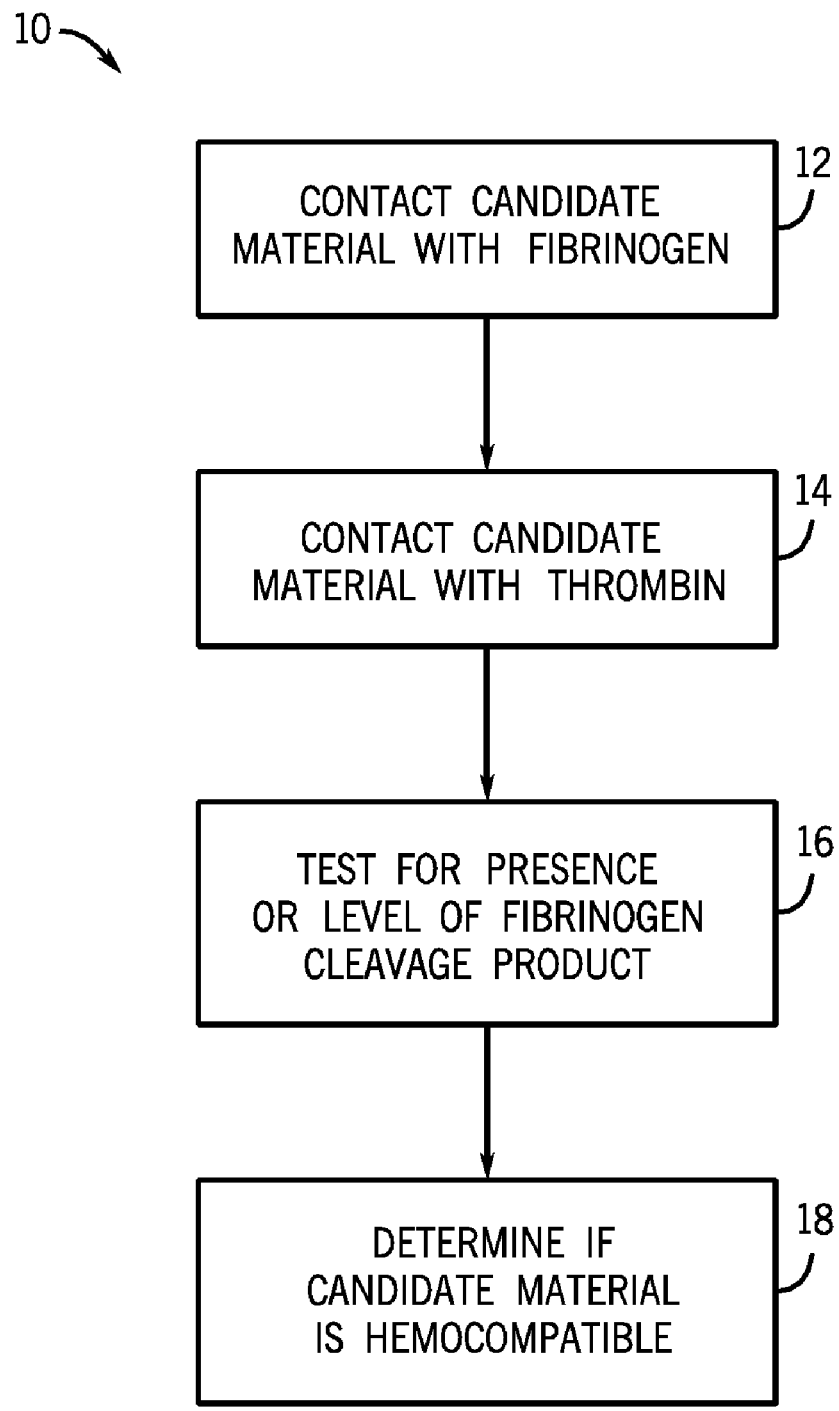
FIG. 1 is an exemplary process for performing the hemocompatibility screening according to the present techniques.

FIG. 1 is an exemplary process 10 for determining the hemocompatibility of a candidate material in accordance with the present technique. In step 12, a candidate material is exposed to fibrinogen. In certain embodiments, the candidate material may be a polymer, a metal and/or metal alloy, a ceramic, a biological material, or any combination thereof.

For example, the candidate material may include silicone, polyurethane, polycarbonates, polyester and polyethylene, biodegradable polymers, bioactive polymers, hydrogels, biopolymers, titanium, stainless steel, or chromium steel. The candidate material may be in any suitable form, such as a gel, foam, layer, strip, well, multi-well, suspension, membrane, or coating. It is envisioned that the present techniques may also be appropriate for testing candidate materials in a high-throughput manner. In such embodiments, a number of candidate materials may be tested simultaneously in, for example, multi-well plates or other suitable testing modalities. In such embodiments, fibrinogen may be applied to at least 10, at least 100, or at least 1000 different samples simultaneously.

The fibrinogen may also be in any suitable form. In certain embodiments, the fibrinogen may be human fibrinogen, recombinant fibrinogen, or fibrinogen from any appropriate source. In certain embodiments, it is envisioned that the fibrinogen is in a suitable buffer. The candidate material may be contacted with the fibrinogen for any appropriate length of time. For example, the fibrinogen may be contacted with the candidate material for at least ten minutes, at least one hour, at least six hours, at least 12 hours, or at least several days. In certain embodiments, after the candidate material has been exposed to fibrinogen, the material may be washed to remove any fibrinogen that is not adsorbed into the material.

In step 14, the candidate material, after exposure to fibrinogen, is contacted with thrombin for a suitable length of time to allow cleavage of any accessible fibrinogen. Fibrinogen that has been adsorbed onto certain candidate materials may change conformation, which may alter the ability of thrombin to cleave the fibrinogen and create fibrinogen cleavage products. Thrombin may be from any suitable source, and may be administered in any form in which the enzyme has sufficient activity to cleave fibrinogen. For example, thrombin in a suitable buffer may be applied to the candidate material. In certain embodiments, the thrombin may be contacted with the candidate material for at least ten minutes, at least one hour, at least six hours, at least 12 hours, or at least several days.

In step 16, the candidate material may be tested for the presence or levels of one or more fibrinogen cleavage products that have been generated from thrombin cleavage. Thrombin cleaves fibrinogen to release cleavage products fibrinopeptide A and fibrinopeptide B from the N-termini of fibrinogen chains Aα and Bβ, respectively. Such testing may involve testing a liquid sample removed from, for example, a test well containing the candidate material, or testing the candidate material directly.

In certain embodiments, testing for fibrinogen cleavage products may include the use of a specific binder for one or more fibrinogen cleavage products. As used herein, the term "specific binding" refers to the binding affinity of one molecule for another. The molecules may have areas on their surfaces or in cavities giving rise to specific recognition between the two molecules arising from one or more of electrostatic interactions, hydrogen bonding, or hydrophobic interactions. A binder may specifically bind to a fibrinogen cleavage product. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, or haptens.

In certain embodiments, the specific binder may include or otherwise be associated with a signal generator. As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, an electrical signal, or a radioactive signal. Examples of signal generators include one or more of a chromophore, a fluorophore, an enzyme, or a radioactive label. In one embodiment, a signal generator may include a probe. As used herein, the term "probe" refers to an agent including a binder and a signal generator. In certain embodiments, the probe may be a target marker. In some embodiments, the binder and the signal generator are embodied in a single entity. The binder and the signal generator may be attached directly (e.g., via a fluorescent molecule incorporated into the binder) or indirectly (e.g., through a linker, which may include a cleavage site) and applied to the biological sample in a single step.

In alternative embodiments, the binder and the signal generator are embodied in discrete entities (e.g., a primary antibody capable of binding a target and a signal generator-labeled secondary antibody capable of binding the primary antibody). When the binder and the signal generator are separate entities, they may be contacted with the test sample, for example a test sample including the candidate material or a liquid sample from a well containing the candidate material, in a single step or multiple steps. For example, in a certain embodiment, it may be appropriate to perform an enzyme-linked immunosorbent assay (ELISA) on the test sample. ELISA assays may include using a secondary antibody that includes a signal generator. The amount of fibrinogen cleavage product in the sample is related to the strength of the signal emitted by the signal generator. Methods of measuring the signal depend on the nature of the label and are known in the art. In certain embodiments, immunoassays such as ELISA may employ signal generators that include radionuclides (e.g., $^{125}I$, $^{131}I$, $^{35}S$, $^{3}H$, or $^{32}P$), enzymes (e.g., alkaline phosphatase, horseradish peroxidase, luciferase, or .beta.-glactosidase), fluorescent moieties or proteins (e.g., fluorescein, rhodamine, phycoerythrin, GFP, or BFP), or luminescent moieties (e.g., quantum dots).

In step 18, based on the results of the testing for the presence or levels of the fibrinogen cleavage product, a determination may be made if a candidate material is hemocompatible. In certain embodiments, a hemocompatible material may be marked by the presence or absence of a fibrinogen cleavage product. In other embodiments, a threshold concentration(s) of one or more fibrinogen cleavage products can be established, and the level of the product in a test sample can be compared to the threshold level(s) associated with hemocompatibility or different degrees of hemocompatibility. In still other embodiments, the level(s) of fibrinogen cleavage products in test samples may be compared to those of references materials, tested prior to, in parallel with, or subsequently to, the test samples in order to obtain a relative hemocompatibility for the test samples.

With the forgoing in mind, the following examples provide specific embodiments in which the present techniques have been applied. In one embodiment, candidate materials were tested for hemocompatibility according to the following protocol. Human fibrinogen (catalog #F 3879 from Sigma-Aldrich, St. Louis, Mo.) was dissolved in 50 mM $Na_2HCO_3$ buffer, pH 8.3 at a concentration of 1.2 mg/mL based on OD 280 nm measurement (with an extinction coefficient of 15.1). For testing, aliquots of frozen fibrinogen solution were thawed and diluted with phosphate buffered saline (PBS) to 300 µg/mL. Samples of the candidate materials to be tested were molded into wells of a 96-well plate. Each candidate material was tested in at least three replicate wells. Before adding the fibrinogen to the wells, the wells containing the test samples were rinsed with PBS. The 300 μg/mL fibrinogen solution was added to the wells at 70 μl/well. After incubation of the test samples in the fibrinogen solution for 30 minutes, the fibrinogen solution was removed and the wells were washed with PBS five times per well to remove any fibrinogen that had not been adsorbed. Reconstituted human thrombin (catalog #T 9010 from Sigma-Aldrich, St. Louis, Mo.) in solution (4 units/mL) was added to each well at 100 μl/well at 37° C. for one hour.

Figure 2:
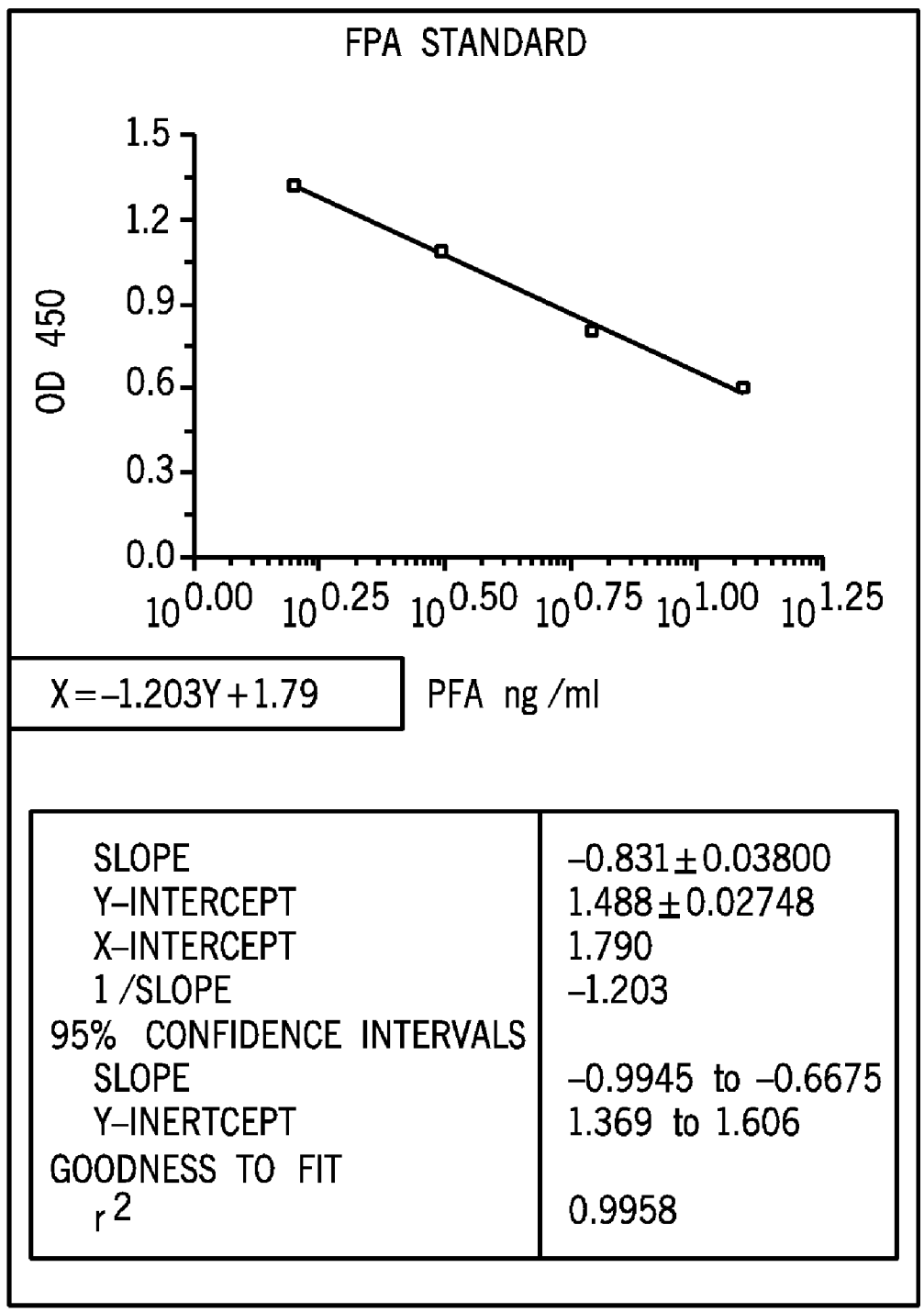
FIG. 2 is a representative standard curve for FPA.

To test for the presence of FPA, 50 μl of solution was removed from each testing well and placed into wells on a new plate. Subsequently, 50 μl of anti-FPA Ab and 130 μl of sample dilution buffer (Imuclone® FPA ELISA Kit, catalog #635 from American Diagnostica Inc., Stamford, Conn.) were added to these wells and allowed to incubate at room temperature for one hour. The antibody mixture from each well was transferred to a separate ELISA microwell assay strip (Imuclone® FPA ELISA Kit, catalog #635 from American Diagnostica Inc., Stamford, Conn.) and incubated at room temperature for an hour. The microwell strips were washed five times in washing buffer (Imuclone® FPA ELISA Kit, catalog #635 from American Diagnostica Inc., Stamford, Conn.). After washing, anti-rabbit IgG-HRP conjugate was added to each well (200 μl) and incubated for one hour at room temperature. The strips were then washed five times in washing buffer. TMB substrate (200 μl) was added to the strips and incubated at room temperature for five minutes. To stop the reaction, 0.45M $H_2SO_4$ (50 μl) was added each well. Then, the optical density of each sample was measured at 450 nm with an ELISA plate reader. Results were calculated using an equation derived from a standard curve of FPA concentration (FIG. 2) at 450 nm.

Figure 3:
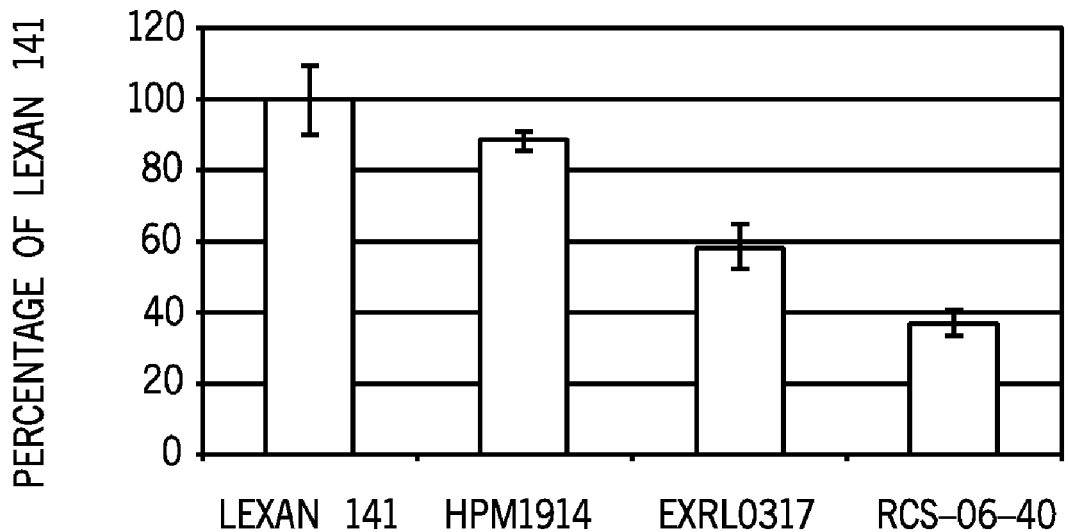
FIG. 3 shows the results for FPA concentration according to the present techniques.
Figure 4:
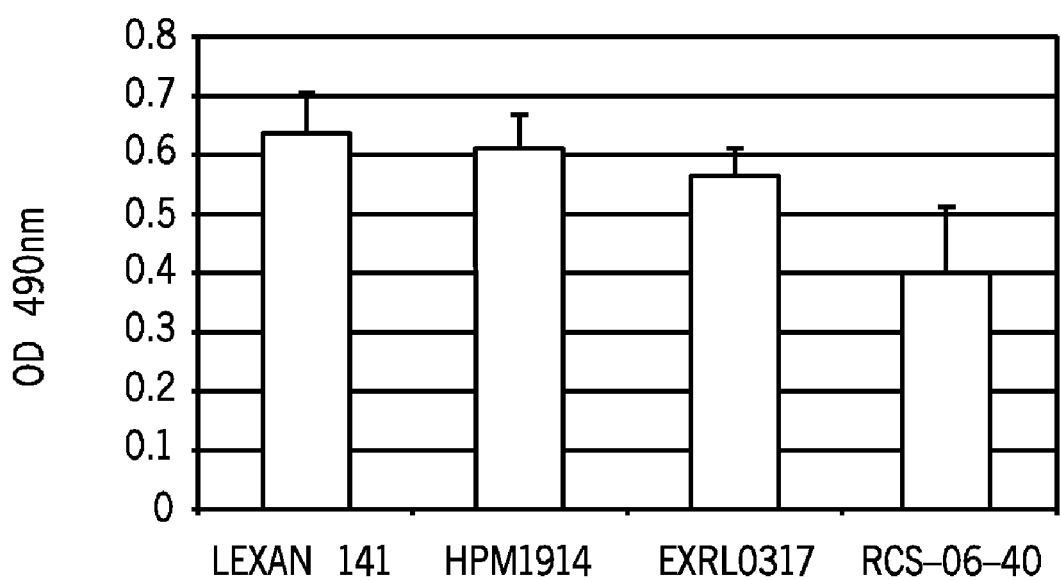
FIG. 4 shows the results for a platelet adhesion test according to the present techniques.
Figure 5:
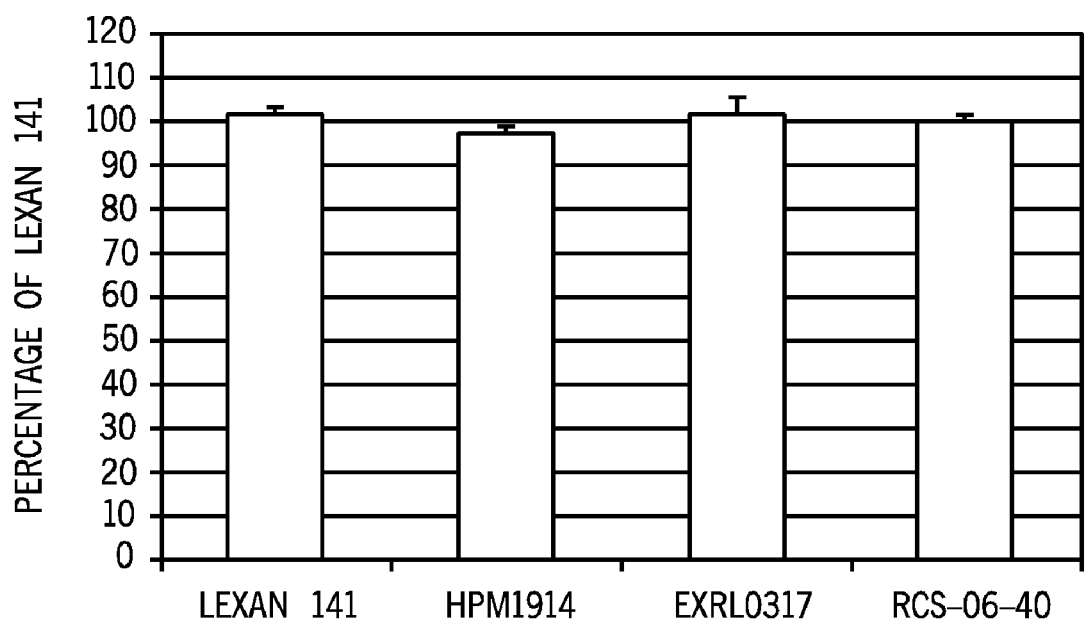
FIG. 5 shows the results for a fibrinogen adsorption test.
Figure 6:
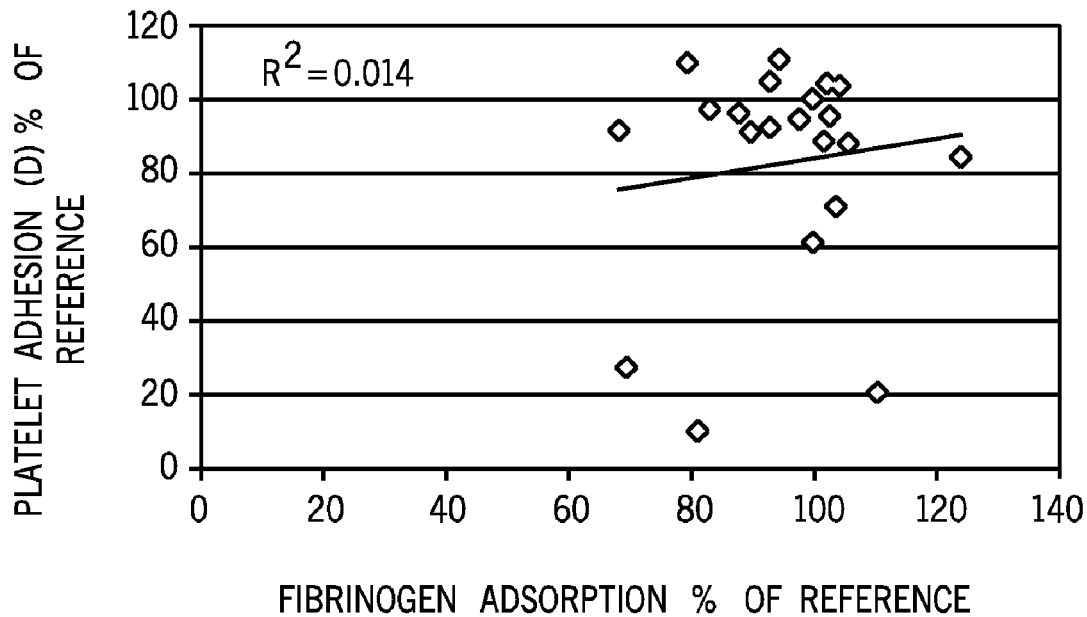
FIG. 6 is a graph showing the lack of correlation between platelet adhesion and a prior technique for measuring fibrinogen adsorption.
Figure 7:
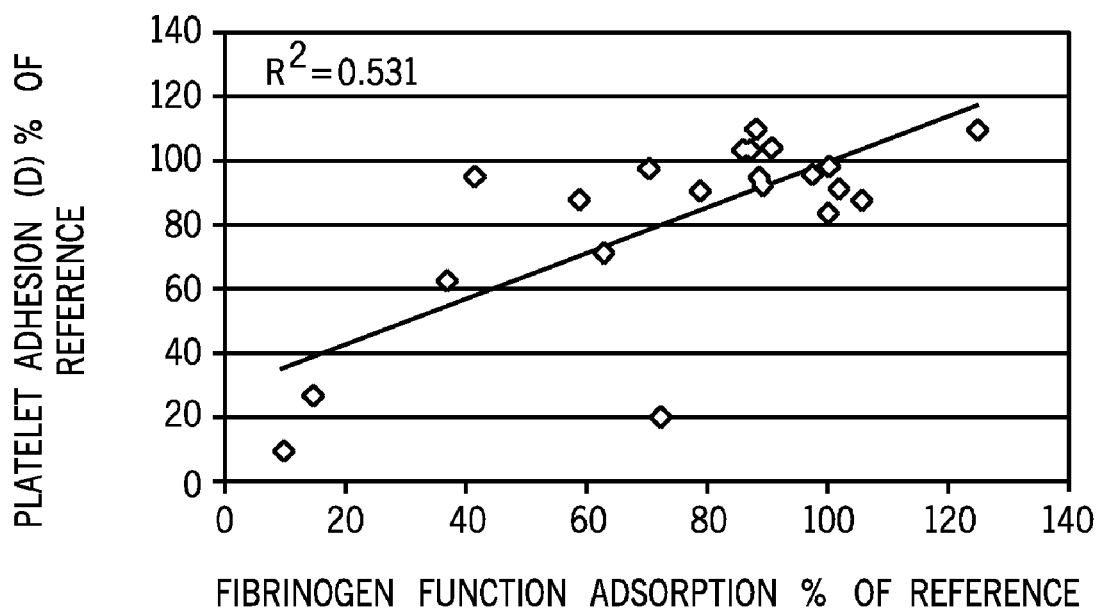
FIG. 7 is a graph showing the correlation between platelet adhesion and FPA concentration according to the present techniques.

FIG. 3 shows a graph of the FPA concentration of 4 different materials as a percentage of one of the four materials, Lexan 141. When compared to a study of platelet adhesion for the same four materials (FIG. 4), platelet adhesion correlated with FPA concentration, i.e. lower FPA correlated with lower platelet adhesion. When compared to a study of fibrinogen adsorption for the same four materials using a traditional antibody-based fibrinogen adsorption quantification assay (FIG. 5), there was no correlation between fibrinogen adsorption and platelet adhesion or FPA concentration. These results are summarized in FIG. 6, which shows a lack of correlation between platelet adhesion and fibrinogen adsorption, and FIG. 7, which shows correlation between platelet adhesion and FPA concentration.

While only certain features of the invention have been illustrated and described herein, many modifications and changes will occur to those skilled in the art. It is, therefore, to be understood that the appended claims are intended to cover all such modifications and changes as fall within the true spirit of the invention. Further, it is envisioned that the hemocompatible materials as provided herein may be used in any appropriate medical device, such as stents, artificial hearts, pacemakers, valves, joints, catheters, membranes, implants, grafts, artificial organs, vessels, or tubing.

The invention claimed is:

1. A method of screening a candidate material for hemocompatibility comprising:
   (1) contacting a candidate material with fibrinogen;
   (2) contacting the candidate material from step (1) with thrombin;
   (3) determining a presence or level of a fibrinogen cleavage product from step (2); and
   determining if the candidate material is hemocompatible based on the presence or level of the fibrinogen cleavage product.

2. The method of claim 1, wherein the fibrinogen cleavage product comprises fibrinopeptide A.

3. The method of claim 1, wherein the fibrinogen cleavage product comprises fibrinopeptide B.

4. The method of claim 1, wherein determining the presence or level of the fibrinogen cleavage product comprises using an antibody specific for the fibrinogen cleavage product.

5. The method of claim 1, wherein determining the presence or level of the fibrinogen cleavage product comprises performing an enzyme-linked immunosorbent assay.

6. The method of claim 1, comprising removing a liquid sample from a receptacle containing the candidate material.

7. The method of claim 6, wherein determining the presence or level of the fibrinogen cleavage product comprises contacting the liquid sample with an antibody specific for the fibrinogen cleavage product.

8. The method of claim 6, wherein determining the presence or level of the fibrinogen cleavage product comprises performing an enzyme-linked immunosorbent assay.

9. A method of screening a candidate material a material for hemocompatibility comprising:
   (1) adsorbing fibrinogen with a candidate material;
   (2) cleaving the fibrinogen from step (1) with thrombin to yield a fibrinogen cleavage product;
   determining a presence or level of conformational change in fibrinogen based on a presence or level of the fibrinogen cleavage product from step (2); and
   (4) determining if the candidate material is hemocompatible based on the presence or level of conformational change in fibrinogen.

10. The method of claim 9, wherein the fibrinogen cleavage product comprises fibrinopeptide A.

11. The method of claim 9, wherein the fibrinogen cleavage product comprises fibrinopeptide B.

12. The method of claim 9, comprising the additional steps of binding the fibrinogen cleavage product with a signal generator and detecting the signal emitted by the signal generator, wherein the signal generator is associated with a primary or secondary antibody.

13. A high-throughput screening method for hemocompatiblity comprising:
   (1) contacting a plurality of candidate materials with fibrinogen;
   (2) contacting the plurality of candidate materials from step (1) with thrombin;
   (3) determining a presence or level of a fibrinogen cleavage product for each of the plurality of candidate materials from step (2); and
   (4) which of the plurality of candidate materials are hemocompatible based on the presence or level of the fibrinogen cleavage product.

14. The method of claim 13, wherein the fibrinogen cleavage product comprises fibrinopeptide A.

15. The method of claim 13, wherein the fibrinogen cleavage product comprises fibrinopeptide B.

16. The method of claim 13, wherein determining the presence or level of the fibrinogen cleavage product comprises performing an enzyme-linked immunosorbent assay.

17. The method of claim 13, comprising removing a respective liquid sample from a plurality of receptacles each containing a respective candidate material.

18. The method of claim 17, wherein determining a presence or level of a fibrinogen cleavage product comprises performing an enzyme-linked immunosorbent assay on each liquid sample.

19. The method of claim 13, wherein the plurality of candidate materials comprises at least 100 materials.

20. A method of making a hemocompatibility medical device comprising:
prov14ding a hemocompatible material, wherein the hemocompatible material is identified by:
(1) contacting a candidate material with fibrinogen;
(2) contacting the candidate material from step (1) with thrombin;
(3) determining a presence or level of a fibrinogen cleavage product from step (2);
and determining if the candidate material is hemocompatible based on the presence or level of the fibrinogen cleavage product; and
(4) forming a medical device from the hemocompatible material identified in step (3).

* * * * *